(12) United States Patent
Potratz

(10) Patent No.: US 6,226,539 B1
(45) Date of Patent: May 1, 2001

(54) PULSE OXIMETER HAVING A LOW POWER LED DRIVE

(75) Inventor: R. Stephen Potratz, Overland Park, KS (US)

(73) Assignee: Mallinckrodt, Inc., Hazelwood, MI (US)

( * ) Notice: Subject to any disclaimer, the term of this patent is extended or adjusted under 35 U.S.C. 154(b) by 0 days.

(21) Appl. No.: 09/320,145

(22) Filed: May 26, 1999

(51) Int. Cl.[7] ................................................ A61B 5/00
(52) U.S. Cl. ................................. 600/323; 356/41
(58) Field of Search .................................. 600/323, 322, 600/310, 326, 473, 476, 39, 41

(56) References Cited

U.S. PATENT DOCUMENTS

| | | | |
|---|---|---|---|
| 5,590,652 | * | 1/1997 | Inai ........................................ 600/323 |
| 5,795,292 | * | 8/1998 | Lewis et al. ......................... 600/323 |
| 5,820,550 | * | 10/1998 | Polson et al. ........................ 600/323 |
| 5,974,338 | * | 10/1999 | Asano et al. ........................ 600/323 |
| 5,983,122 | * | 11/1999 | Jarman et al. ....................... 600/323 |
| 5,995,855 | * | 11/1999 | Kiani et al. .......................... 600/323 |

* cited by examiner

*Primary Examiner*—Eric F. Winakur
*Assistant Examiner*—Brian Szmal
(74) *Attorney, Agent, or Firm*—Hovey, Williams, Timmons & Collins

(57) ABSTRACT

A photometer (10) includes a light source (12) operable to direct light toward a sample (14), a detection circuit (16) operable to detect the light after it has passed through the sample, and a drive circuit (18) for powering the light source. The drive circuit includes an input (20) for coupling with a source of power and energy storage circuitry (22) coupled with the input. The energy storage circuitry is operable to store energy from the source of power when switched to a charging state and to deliver current to the light source in a ramped manner when switched to a discharge state so that the current peaks at a selected time. The drive circuit delivers a controlled amount of current to the light source that peaks only after the detection circuit has settled so that power is not wasted at the startup of the oximeter.

20 Claims, 1 Drawing Sheet

PULSE OXIMETER HAVING A LOW POWER LED DRIVE

BACKGROUND OF THE INVENTION

1. Field of the Invention

Figure 1:
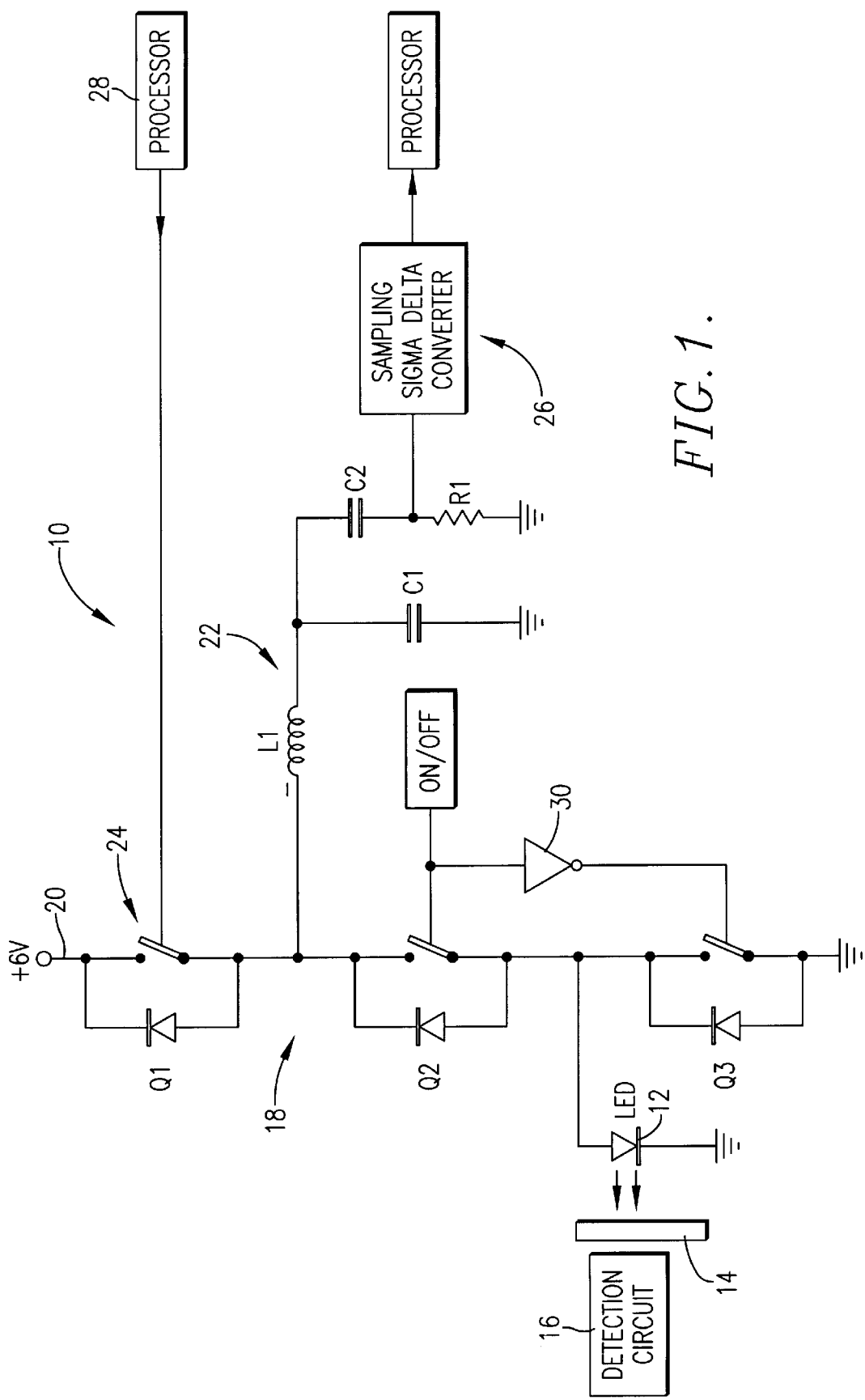

The present invention relates to photometers such as pulse oximeters. More particularly, the invention relates to a pulse oximeter having a low power drive for efficiently powering the light source of the oximeter.

2. Description of the Prior Art

Oximeters are used to measure the oxygenated fraction of hemoglobin in blood by analyzing the absorption of light transmitted through or reflected from the blood. A typical oximeter includes a light source such as a light emitting diode (LED) that generates and directs light toward a sample, a drive circuit for powering the LED, and a detection circuit that detects and analyzes the light from the LED after it has passed through the sample. After the LED is turned on, the detection circuit must "settle" before an accurate reading can be made. This results in inefficient power usage in existing oximeters because power delivered to the LED is wasted while the detection circuit is settling and because much of the current generated by the LED drive circuitry dissipates in resistive components of the circuitry.

OBJECTS AND SUMMARY OF THE INVENTION

The present invention solves the above-described problems and provides a distinct advance in the art of oximeters and other photometers. More particularly, the present invention provides a pulse oximeter having a low power LED drive that uses power more efficiently, especially during the settling time of the oximeter.

The oximeter of the present invention broadly includes a light source operable to direct light toward a sample, a detection circuit operable to detect the light after it has passed through the sample, and a drive circuit for powering the light source. The drive circuit is configured to deliver a controlled amount of current to the LED that peaks only after the detection circuit has settled so that power is not wasted at the startup of the oximeter. The drive circuit is also configured to temporarily store and then deliver all of the energy from a source of power to the LED without dissipating much of the energy in resistive components.

The drive circuit includes an input for coupling with a source of power and energy storage circuitry coupled with the input. The energy storage circuitry is operable to store energy from the source of power when switched to a charging state and to deliver current to the light source in a ramped manner when switched to a discharge state so that the current peaks at a selected time.

BRIEF DESCRIPTION OF THE DRAWING FIGURES.

A preferred embodiment of the present invention is described in detail below with reference to the attached drawing figure, wherein:

FIG. 1 is an electrical schematic diagram of an oximeter constructed in accordance with a preferred embodiment of the present invention.

DETAILED DESCRIPTION OF THE PREFERRED EMBODIMENTS

Turning now to FIG. 1, an oximeter 10 constructed in accordance with a preferred embodiment of the invention is illustrated. The oximeter broadly includes a light source 12 operable to direct light toward a sample 14, a detection circuit 16 operable to detect the light after it has passed through the sample, and a drive circuit generally referred to by the numeral 18 for powering the light source. The sample may be a person's finger or other body part or a blood sample withdrawn from a patient.

The light source 12, which is conventional, is preferably a light emitting diode (LED), but may be any other light source used in photometers. The detection circuit 16, which is also conventional, may include any light sensitive sensor and detection circuitry used with oximeters or other photometers.

The drive circuit 18 is coupled with the light source 12 and a source of power such as a six-volt battery and is operable to power the light source. The drive circuit broadly includes an input 20, energy storage circuitry generally referred to by the numeral 22, switching circuitry generally referred to by the numeral 24, and current measuring circuitry generally referred to by the numeral 26.

The input 20 is configured for coupling with the source of power for delivering current from the power source to the energy storage circuitry 20 as described below. The input may also be coupled with a current limiting resistor (not shown) and one or more capacitors (not shown) for limiting the current delivered to the energy storage circuitry.

In accordance with one aspect of the present invention, the energy storage circuitry 22 is configured to store energy from the source of power when the circuitry is switched to a charging state and to deliver current to the light source 12 in a controlled manner when switched to a discharge state. The storage circuitry preferably includes a capacitor C1 and an inductor L1 connected as illustrated. As described in more detail below, C1 stores a charge delivered from the source of power when the energy storage circuitry is switched to its charging state and discharges the charge to the light source when the energy storage circuitry is switched to its discharge state. L1 is wired between the input 20 and C1 and is configured to charge C1 when the energy storage circuitry is switched to its charging state and to deliver the charge from C1 to the light source when the energy storage circuitry is switched to its discharge state.

C1 and L1 are sized to form a tuned circuit that resonates such that a partial half wave of current is delivered to the light source 12 and allowed to peak once the detection circuit 16 has settled. In one embodiment, C1 has a value of 16 v, 10 uF and L1 has a value of 470 uH.

The switching circuitry 24 preferably includes a transistor Q1, a transistor Q2 and a transistor Q3. Q1, Q2, and Q3 together switch the energy storage circuitry 22 between its charging state and its discharge state to selectively store energy in the circuitry 22 and to then deliver the stored energy to the light source 12.

Q1 is wired between the input 20 and the energy storage circuitry 21 to selectively switch energy from the power source to the energy storage circuitry for charging the circuitry. Q1 is preferably turned on and off by a processor 28, which can be programmed to turn Q1 on for a selected time period for controlling the amount of energy delivered to the energy storage circuitry from the power source.

Q2 is wired between the energy storage circuitry 22 and the light source 12 to selectively switch current stored in the energy storage circuitry to the light source. Q3 is wired between the energy storage circuitry and ground to selectively ground the light source. Q2 and Q3 are preferably switched on and off by the processor 28 or by another controller. As illustrated, the input to Q3 is inverted by an inverter 30 whereas the input to Q2 is not; therefore, whenever Q2 is switched on, Q3 is switched off, and vice versa.

The current measuring circuitry 26 is coupled with the energy storage circuitry 22 and is operable for measuring the amount of current that is delivered to the light source 12. This current reading is then used as a feedback for use in calibrating the amount of time that Q1 is switched on while charging the energy storage circuitry. The current measuring circuitry preferably includes a capacitor C2, a resistor R1, a sampling sigma delta convertor 32, and a processor 34. C2 preferably has a rating of 50 v, 0.01 uF and R1 preferably has a rating of 3.01K ohm. Operation In operation, the processor 28 initially switches Q1 and Q2 off (open) and switches Q3 on (closed). Because Q1 and Q2 are off, the power source connected to the input 20 is not delivering energy to the energy storage circuitry 22, and the energy storage circuitry is not delivering a charge to the light source. Because Q3 is switched on, both lines to the light source are grounded so that no current is being delivered to the light source.

When it is desired to operate the oximeter 10, the processor 28 turns on Q1 for a very brief period to transfer energy from the power source to the energy storage circuitry 22 through L1. The amount of energy transferred to C1 is directly related to how long Q1 is turned on. Thus, the processor 28 is programmable to provide a selected width pulse to Q1 to control the amount of energy delivered to C1. In preferred forms, the processor switches Q1 on for approximately 5 to 10 uS.

Once the desired amount of energy has been stored in the energy storage circuitry 22, the processor 28 switches Q1 off to stop the delivery of energy to the energy storage circuitry. However, a magnetic field, which builds up in L1 while Q1 is on, continues to transfer energy to C1 after Q1 is turned off. This is because when Q1 turns off, the negative side of L1 is grounded through the substrate diode of Q2 and through Q3, which is still on. Therefore, the collapsing magnetic field on L1 transfers all of its energy (except the energy that is lost across the diode of Q2) to C1.

After the energy storage circuitry 22 has become fully charged, the switching circuitry 24 may be selectively operated to discharge the stored energy to the light source 12 for illuminating the light source. Specifically, the processor 28 turns Q2 on and turns Q3 off so that L1 and C1 are connected to the light source. This causes the charge on C1 to discharge to the light source through L1 and Q2. Because L1 and C1 form a tuned circuit as described above, a partial, sinusoidal half wave of current is delivered to the light source. The drive circuit 18 is configured so that the current peaks at a selected time after the energy storage circuitry begins to discharge to the light source. This allows the current delivered to the light source to peak at the same time the detection circuitry 16 has settled so that a minimal amount of energy is wasted during the settling time of the detection circuitry.

Once the energy storage circuitry 22 discharges its energy to the light source 12, the above charging and discharging steps can be repeated when it is desired to once again operate the oximeter.

To deliver the optimum amount of current to the light source 12 to achieve the above-described results, the programmable width pulse delivered to Q1 by the processor 28 must be selected. Because the optimum amount of current delivered to the light source is dependent on the characteristic voltage drop of the light source itself, the voltage drop of the light source must be measured to calibrate the width of the pulse delivered to Q1. This is done by measuring the current delivered from the energy storage circuitry 22 to the light source that results from a given pulse width.

This current measurement is derived from the current flowing through C2 which, with R1, is in parallel with C1. Because the value of R1 is so low it can be essentially ignored, C2 is essentially in parallel with C1. Furthermore, because C1 is 1,000 times larger than C2, the current flowing through C2 is 1/1000 the current flowing through C1. R1 converts the current through C2 to a voltage that can be measured by the sampling sigma delta convertor 32 and the processor 34. The measured voltage is then used as feedback to the processor 28 to vary the width if the pulse delivered to Q1 to selectively vary the amount of energy that is delivered to the energy storage circuitry 22 and that is eventually discharged to the light source 12.

Once properly calibrated, the drive circuitry 18 delivers a controlled amount of current to the light source 12 that peaks only after the detection circuit 16 has settled. This reduces the amount of power that is wasted by the light source during the initial settling time of the detection circuit. Additionally, because the energy storage circuitry 22 includes a capacitor and an inductor but no resistive components, very little power is dissipated during the charging and discharge states of the circuitry.

Although the invention has been described with reference to the preferred embodiment illustrated in the attached drawing figure, it is noted that equivalents may be employed and substitutions made herein without departing from the scope of the invention as recited in the claims. For example, although the drive circuit of the present invention has been illustrated and described as being used with a pulse oximeter, it may also be used with other photometer devices for driving the light sources thereof.

Having thus described the preferred embodiment of the invention, what is claimed as new and desired to be protected by Letters Patent includes the following:

1. A photometer comprising:
   a light source operable to direct light toward a sample;
   a detection circuit operable to detect the light after it has passed through the sample; and
   a drive circuit for powering the light source, the drive circuit including
      an input for coupling with a source of power, and
      energy storage circuitry coupled with the input and operable to store energy from the source of power when switched to a charging state and to deliver current to the light source in a ramped manner so that the current peaks at a selected time when switched to a discharge state.

2. The photometer as set forth in claim 1, the drive circuit further including switching circuitry for selectively switching the energy storage circuitry between the charging state and discharge state.

3. The photometer as set forth in claim 1, the energy storage circuitry including:
   a capacitor for storing a charge when the energy storage circuitry is switched to the charging state and for discharging the charge to the light source when the energy storage circuitry is switched to the discharge state; and
   an inductor wired between the input and the capacitor for charging the capacitor when the energy storage circuitry is switched to the charging state and for delivering the charge from the capacitor to the light source when the energy storage circuitry is switched to the discharge state.

4. The photometer as set forth in claim 3, wherein the capacitor and the inductor form a tuned circuit operable to resonate such that a partial half wave of current is allowed to peak while the energy storage circuitry is in the discharge state.

5. The photometer as set forth in claim 2, the switching circuitry including a first transistor wired between the input and the energy storage circuitry for switching energy from the power source to the energy storage circuitry.

6. The photometer as set forth in claim 5, the switching circuitry further including a second transistor wired between the energy storage circuitry and the light source for switching current from the energy storage circuitry to the light source.

7. The photometer as set forth in claim 1, the light source comprising a light emitting diode.

8. A drive circuit for powering a light source in a photometer, the drive circuit comprising:
an input for coupling with a source of power; and
energy storage circuitry coupled with the input and operable to store energy from the source of power when switched to a charging state and to deliver current to the light source in a ramped manner so that the current peaks at a selected time when switched to a discharge state.

9. The drive circuit as set forth in claim 8, further including switching circuitry for selectively switching the energy storage circuitry between the charging state and discharge state.

10. The drive circuit as set forth in claim 8, the energy storage circuitry including:
a first capacitor for storing a charge when the energy storage circuitry is switched to the charging state and for discharging the charge to the light source when the energy storage circuitry is switched to the discharge state; and
an inductor wired between the input and the first capacitor for charging the first capacitor when the energy storage circuitry is switched to the charging state and for delivering the charge from the first capacitor to the light source when the energy storage circuitry is switched to the discharge state.

11. The photometer as set forth in claim 10, wherein the capacitor and the inductor form a tuned circuit operable to resonate such that a partial half wave of current is allowed to peak while the energy storage circuitry is in the discharge state.

12. The photometer as set forth in claim 9, the switching circuitry including a first transistor wired between the input and the energy storage circuitry for switching energy from the power source to the energy storage circuitry.

13. The photometer as set forth in claim 12, the switching circuitry further including a second transistor wired between the energy storage circuitry and the light source for switching current from the energy storage circuitry to the light source.

14. The photometer as set forth in claim 8, the light source comprising a light emitting diode.

15. The photometer as set forth in claim 10, further including a second capacitor coupled with the first capacitor for measuring the current delivered to the light source when the energy storage circuitry is switched to the discharge state.

16. A photometer comprising:
a light source operable to direct light toward a sample;
a detection circuit operable to detect the light after it has passed through the sample; and
a drive circuit for powering the light source, the drive circuit including
an input for coupling with a source of power,
switching circuitry for selectively switching the drive circuit between a charging state and a discharging state,
a capacitor for receiving and storing a charge when the drive circuit is in the charging state and for discharging the charge to the light source when the drive circuit is in the discharging state, and
an inductor for charging the capacitor when the drive circuit is in the charging state and for delivering the charge from the capacitor to the light source when the drive circuit is in the discharging state.

17. The photometer as set forth in claim 16, the inductor and capacitor operating together to restrict delivery of the charge until a predetermined time period has passed following switching of the drive circuit to a discharging state.

18. The photometer as set forth in claim 17, delivery of the charge being restricted to a ramp function peaking a predetermined time period after switching of the drive circuit to a discharging state.

19. A photometer comprising:
a light source operable to direct light toward a sample, the light source having a voltage drop value;
a detection circuit operable to detect the light after it has passed through the sample;
a drive circuit coupled with the light source and the microprocessor and operable to power the light source, the drive circuit including
an input for coupling with a source of power,
switching circuitry for selectively switching the drive circuit between a charging state and a discharging state, with the charging state being limited in duration to a charging time, and
a storage capacitor for storing a charge when the drive circuit is in the charging state and for discharging the charge to the light source when the photometer is in the discharging state; and
a compensation circuit coupled to the drive circuit and the light source and operable to determine the voltage drop value of the light source and to adjust the charging time of the charging state to compensate there for.

20. A method for delaying peak charge delivery to a light source element of a photometer, the light source element having a voltage drop value, the method comprising the steps of:
determining the length of a desired delay period;
selecting and configuring a capacitive energy storage element and an inductive control element based on the length of the desired delay period;
determining the voltage drop value of the light source element;
charging the capacitive energy storage element with a charging pulse, the charging pulse having a pulse width based on the determined voltage drop value of the light source element; and
discharging the capacitive storage element through the inductive control element to result in delaying the peak charge delivery to the light source by the length of the desired delay period.

* * * * *